US00PP35393P3

(12) United States Plant Patent
Olesen

(10) Patent No.: US PP35,393 P3
(45) Date of Patent: Sep. 26, 2023

(54) ROSE PLANT NAMED 'POULCAS066'

(50) Latin Name: *Rosa hybrida*
Varietal Denomination: Poulcas066

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,624

(22) Filed: Sep. 13, 2022

(65) Prior Publication Data

US 2023/0116919 P1 Apr. 13, 2023

(30) Foreign Application Priority Data

Sep. 24, 2021 (QZ) ..... PBR 2021/2367

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749; A01H 5/02
See application file for complete search history.

*Primary Examiner* — Keith O. Robinson

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulcas066'.

This application claims priority to Plant Breeder's Rights Application Number 2021/2367, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulcas066', originated as a single seedling from the stated cross.

The new variety may be distinguished from its male pollen parent and female seed parent primarily by the following characteristics. The male pollen parent plant has pink flowers while the new variety has red flowers. The female seed parent plant has the growth habit of a climber, while the newly claimed plant is a compact floribunda shrub.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcas066' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulcas066' was selected in the spring of 2014 by the inventor as a single plant from the progeny of the aforementioned hybridization.

Asexual reproduction of 'Poulcas066' by rooted cuttings was first done by Mogens N. Olesen in the nursery in Fredensborg, Denmark in July, 2014. This initial and other subsequent asexual propagations conducted in controlled environments have demonstrated that the characteristics of 'Poulcas066' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas066'.

Specifically illustrated in FIG. 1 of the drawings are open flowers viewed from the side and above, flower petals detached revealing reproductive flower parts, sepals detached revealing the shape of the receptacle, and flower buds at various stages of development.

Figure 1:
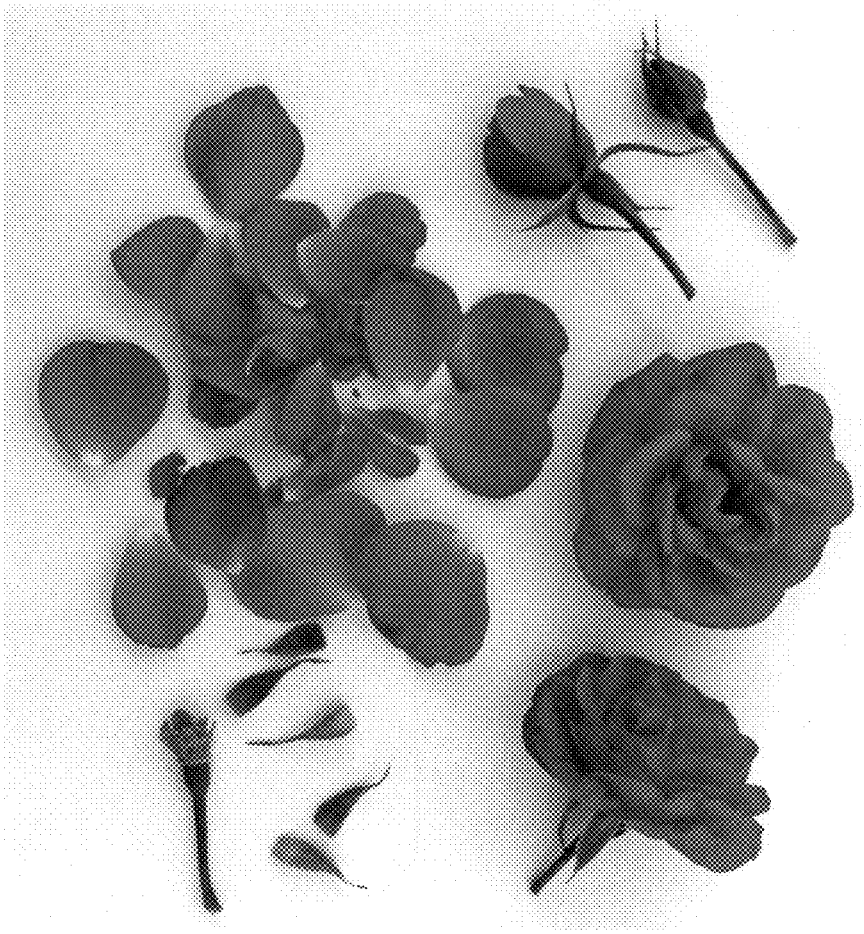
Figure 2:
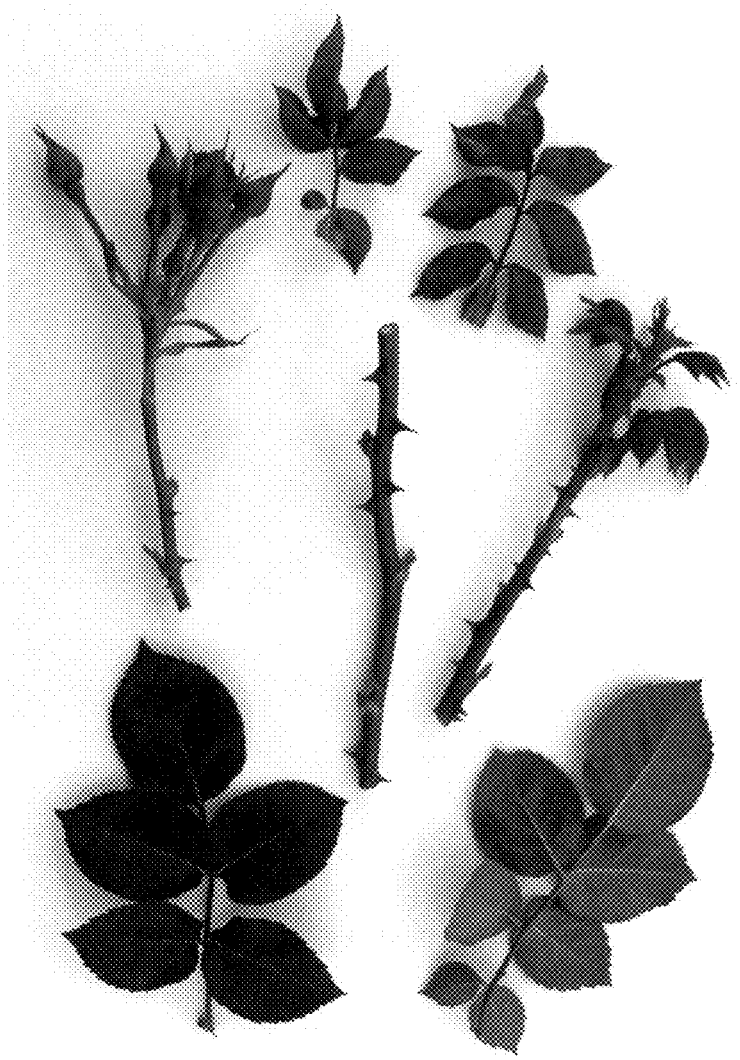

Specifically illustrated in FIG. 2 of the drawings are juvenile leaves, juvenile stems, mature leaves, mature stems, and a cluster of flower buds on a branch.

Plants shown are 2 years of age.

DETAILED DESCRIPTION OF THE VARIETY

The following is a description of 'Poulcas066', as observed in its growth outdoor in Odense Denmark. Observed plants are 18 months of age, and were grown on their own roots in 30 cm containers. Color references are made using The Royal Horticultural Society (London, England) Colour Chart, 2001, except where common terms of color are used.

For a comparison, several physical characteristics of the rose variety 'Poulcas062', U.S. Plant Pat. No. 33,175 are compared to 'Poulcas066'. The claimed plant has a petal count of about 35 petals with a flower diameter of 70 mm. 'Poulcas062' has a petal count of 45 petals and a flower diameter of 75 mm. The general tonality of flower colour for the claimed plant is Red-Purple Group N57A, while the comparison variety 'Poulcas062' is Red-Purple Group 65A and 65B.

FLOWER AND FLOWER BUD

Blooming habit: Continuous.

Flower bud:

- *Size.*—Upon opening, 27 mm in length from base of receptacle to end of bud. Bud diameter is 15 mm.
- *Bud form.*—Ovoid.
- *Bud color.*—As sepals divide petals are Red-Purple Group N57A.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Generally subulate. Apex: Aristate. Base: Flat at union with receptacle.Å.
- *Sepal margin.*—Margins have weak foliaceous appendages on three of the five sepals.
- *Sepal size.*—31 mm long, 7 mm wide.
- *Receptacle.*—Texture: Smooth on upper and lower surface. Size: 11 mm in height, 6 mm wide. Color: Yellow-Green Group 144A. Shape: Globose.
- *Pedicel.*—Surface: Smooth. Length: About 36 mm. Diameter: 2 to 3 mm. Color: Yellow-Green Group 144B with intonations of Greyed-Red Group 180A. Strength: Strong.
- *Peduncle.*—Length: 10 to 15 mm. Diameter: About 3 mm. Color: Yellow-Green Group 144A. Texture: Smooth.

Flower bud development: Flower buds are borne in clusters of 3 to 7 flower buds per stem, developed as a cyme.

Flower bloom:

- *Fragrance.*—Light floral.
- *Duration.*—The blooms have a duration on the plant of approximately 15 days. Petals fall cleanly away from plant after flowers have fully matured.
- *Size.*—Flower diameter is 70 mm when open. Flower depth is 24 mm.
- *Flower shape.*—Rosette, very double flower with many slightly overlapping petals of different sizes.
- *Shape of flower, side view.*—The upper portion is convex. The lower portion is flat.

Petalage: Under normal conditions, flowers have about 35 petals.

General tonality of flower: Open flowers are Red-Purple Group N57A.

Petal color:

- *Upon opening, outer and inner petals.*—Upper surface: Red-Purple Group N57A. Streaks of Red Group 56D at the basal to middle zone. At the basal point of attachment Yellow Group 8C. Lower surface: Red-Purple Group N57A. Streaks of Red Group 56D at the basal to middle zone. At the basal point of attachment Yellow Group 8C.
- *After opening, outer and inner petals.*—Upper surface: Red-Purple Group N57A. At the basal point of attachment Green-White Group 157A. Lower surface: Red-Purple Group N57A. At the basal point of attachment Green-White Group 157A.

Petals:

- *Petal reflex.*—Somewhat reflexed.
- *Margin.*—Entire with occasional small cleft. No undulations.
- *Shape.*—Broad and elliptic. Apex shape: Rounded. Base shape: Acute.
- *Size.*—About 34 mm (l)×36 mm (w).
- *Texture.*—Smooth.
- *Thickness.*—Average.

Petaloids:

- *Size.*—27 mm (l) by 17 mm (w).
- *Quantity.*—About 6.
- *Shape.*—Elliptical with an acute base and rounded apex. Apex of margin has a single cleft.
- *Color.*—Red-Purple Group N57A. At the basal point of attachment Green-White Group 157A.

Reproductive flower parts:

- *Pollen.*—None observed.
- *Anthers.*—Size: 2 mm in length. Color: Yellow-Orange Group 18B. Quantity: 30 on average.
- *Filaments.*—Color: Orange-Red Group N34D and Yellow Group 10A. Length: 5 mm.
- *Pistils.*—Length: 7 mm. Quantity: 27 on average.
- *Stigmas.*—Color: Yellow-White Group 158C.
- *Styles.*—Color: Green-White Group 157A with intonations of Red-Purple Group 58C.
- *Location of stigmas.*—Level in location relative to the length of the filaments and the height of the anthers.
- *Hips.*—None Observed.

PLANT

Plant growth: Upright, bushy. Plants are 50 cm in height, and 53 cm wide.

Stems:

- *Color of juvenile growth.*—Yellow-Green Group 144B with intonations of Greyed-Purple Group 183C.
- *Color of mature growth.*—Yellow-Green Group 146B.
- *Length.*—Canes are about 22 cm from the base of the plant to the flowering portion.
- *Diameter.*—About 7 mm.
- *Internodes.*—On mature canes about 41 mm between nodes.
- *Surface texture.*—Young wood: Smooth. Older wood: Smooth.

Long prickles:

- *Incidence.*—9 prickles per 10 cm of stem.
- *Size.*—Average length of prickles on mature stems is 9 mm.
- *Shape.*—Upper portion is linear. Lower portion is concave.
- *Color.*—Juvenile prickles: Greyed-Red Group 180A. Mature prickles: Greyed-Orange Group 166B.

Plant foliage:

*Compound leaf*.—About 147 mm (l)×100 mm (w).

*Quantity*.—2 leaves per 10 cm of stem on average.

*Leaf bearing angle to the stem*.—45 degrees.

*Color of juvenile foliage*.—Upper side: Yellow-Green Group 146B with shades of Greyed-Orange Group 166A. Lower side: Yellow-Green Group 146B with shades of Greyed-Orange Group 166A.

*Color of mature foliage*.—Upper side: Yellow-Green Group 147A. Lower side: Yellow-Green Group 147B.

Plant leaves and leaflets:

*Stipules*.—Size: 10 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 31 mm. Diameter: 2 mm. Upper surface color: Yellow-Green Group 146A with intonations of Greyed-Orange Group 166A. Lower surface color: Yellow-Green Group 144A.

*Rachis*.—Length: 64 mm. Upper surface color: Yellow-Green Group 146A with intonations of Greyed-Orange Group 166A. Lower surface color:

*Leaflet*.—Quantity: Normally 5 leaflets, occasionally 7. Margins: Serrated. Size: Terminal leaflets are about 60 mm long, 48 mm wide. Shape: Generally elliptical. Base: Rounded. Apex: Mucronate. Texture: Smooth on the upper and lower surface. Thickness: Average. Arrangement: Odd pinnate. Venation: Reticulate. Glossiness: Very glossy on the upper surface.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcas066' substantially as described and illustrated herein.

* * * * *